US008831704B2

(12) United States Patent
Stemmer (10) Patent No.: US 8,831,704 B2
(45) Date of Patent: Sep. 9, 2014

(54) MAGNETIC RESONANCE METHOD AND APPARATUS FOR TRIGGERED ACQUISITION OF MAGNETIC RESONANCE MEASUREMENT DATA

(75) Inventor: Alto Stemmer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 100 days.

(21) Appl. No.: 13/451,014

(22) Filed: Apr. 19, 2012

(65) Prior Publication Data

US 2012/0271155 A1 Oct. 25, 2012

(30) Foreign Application Priority Data

Apr. 21, 2011 (DE) .......................... 10 2011 007 850

(51) Int. Cl.
*A61B 5/055* (2006.01)
*G01R 33/56* (2006.01)
*A61B 5/08* (2006.01)
*G01R 33/567* (2006.01)
*A61B 5/00* (2006.01)

(52) U.S. Cl.
CPC ............ *G01R 33/5607* (2013.01); *A61B 5/055* (2013.01); *A61B 5/0816* (2013.01); *G01R 33/5676* (2013.01); *A61B 5/7285* (2013.01)
USPC ............................ 600/410; 600/407; 600/413

(58) Field of Classification Search
USPC .......................................... 600/407, 410, 413
See application file for complete search history.

(56) References Cited

U.S. PATENT DOCUMENTS

| 2007/0069726 A1 | 3/2007 | Miyoshi |
| 2008/0224699 A1 | 9/2008 | Hughes |
| 2010/0264922 A1 | 10/2010 | Xu |
| 2010/0268062 A1* | 10/2010 | Edelman ....................... 600/410 |
| 2010/0277173 A1 | 11/2010 | Landschuetz et al. |
| 2011/0130644 A1* | 6/2011 | Stemmer ....................... 600/410 |

OTHER PUBLICATIONS

"Comparison of Respiratory Triggering and Gating Techniques for the Removal of Respiratory Artifacts in MR Imaging," Lewis et al., Radiology, vol. 160 (1986) pp. 803-810.

* cited by examiner

*Primary Examiner* — Peter Luong
(74) *Attorney, Agent, or Firm* — Schiff Hardin LLP (57) ABSTRACT

In a magnetic resonance method and apparatus, a) data points of a physiological signal are detected, b) a trigger condition is evaluated depending on the detected physiological data points, c) a preparation module is executed to suppress unwanted signals in the time period in which the trigger condition has not yet been satisfied, d) after satisfying the trigger condition, an acquisition phase of predetermined duration is started, that includes at least two similar preparation modules to suppress unwanted signals and a respective following acquisition module to acquire measurement data, and e) after the acquisition phase, a) through d) are repeated until all desired measurement data have been acquired, with a time interval between two successive preparation modules being the same after a first execution of a preparation module in c) until the end of the acquisition phase in a subsequent d).

13 Claims, 5 Drawing Sheets

MAGNETIC RESONANCE METHOD AND APPARATUS FOR TRIGGERED ACQUISITION OF MAGNETIC RESONANCE MEASUREMENT DATA

BACKGROUND OF THE INVENTION

1. Field of the Invention

The present invention concerns a method to suppress unwanted signal components during an acquisition (triggered via a physiological signal of the examination subject) of magnetic resonance measurement data from an examination subject and a corresponding magnetic resonance apparatus, and a non-transitory computer-readable data storage medium to implement such a method.

2. Description of the Prior Art

The MR technique (MR: magnetic resonance) is a technique known for a few decades with which images of the inside of an examination subject can be generated. As a significantly simplified description, the examination subject is positioned in a comparably strong, static, homogeneous basic magnetic field (field strengths from 0.2 Tesla to 7 Tesla or more) in a magnetic resonance apparatus so that nuclear spins in the subject orient along the basic magnetic field. Radio-frequency excitation pulses are radiated into the examination subject to trigger nuclear magnetic resonance signals, the triggered nuclear magnetic resonance signals are measured (detected), and MR images are reconstructed based thereon. For spatial encoding of the measurement data, rapidly switched magnetic gradient fields are superimposed on the basic magnetic field. The acquired measurement data are digitized and stored as complex numerical values in a k-space matrix. An associated MR image can be reconstructed from the k-space matrix, populated with such values, by means of a multidimensional Fourier transformation. The chronological order of the excitation pulses and the gradient fields to excite the image volume to be measured, for signal generation and for spatial encoding is designated as a sequence (or also as a pulse sequence or measurement sequence).

In magnetic resonance imaging (MRI) of examination regions affected by breathing movement, for example the organs of the thorax and abdomen, the breathing movement can lead to ghosting, blurring, intensity loss and registration errors between images in the reconstructed MR images. These artifacts hinder the identification of findings by a physician on the basis of these MR images and can lead to pathological changes (such as lesions, for example) being overlooked.

Numerous techniques exist in order to reduce artifacts as a result of breathing movement. Some of these techniques can be summarized under what is known as respiratory triggering. For example, such techniques are described in the overview article by Craig E. Lewis et al. "Comparison of Respiratory Triggering and Gating Techniques for the Removal of Respiratory Artifacts in MR Imaging", Radiology 1986; 160:803-810.

Respiratory triggering attempts to synchronize the MR measurement with the respiratory cycle of the freely breathing patient and to limit the measurement to the relatively quiet (i.e. low-movement) phase of the respiratory cycle at the end expiration. For this purpose, the breathing of the patient is detected as a physiological signal with a breathing sensor (for example a pneumatic breathing sensor). After an initial learning phase of the trigger algorithm in which the conditions which should initiate a "trigger" are determined, a "trigger" is thereby generated as soon as the predetermined trigger event (for example a defined phase of the respiratory cycle) is detected.

As a result of the "trigger", the MR sequence acquires a portion of the data (which portion is predetermined in turn) of one or more slices of the examination subject. The "trigger" thus initiates the acquisition of predetermined data in the examination region. After such a predetermined data packet has been acquired, the data acquisition stops automatically until the trigger algorithm generates the next "trigger". A second data packet is thereupon acquired. This workflow is continued until all data of all slices of the examination region to be examined are acquired. A slice means the partial region of the examination region that is excited via a particular selective excitation pulse of the sequence. In two-dimensional (2D) sequence techniques (that are particularly important in connection with the present invention), the examination region is most often divided into one or more groups of slices parallel to one another.

The trigger event is normally selected such that "triggers" are generated during expiration, and such that the data acquisition is limited to the relatively low-movement phase of the respiratory cycle at the end expiration. One trigger event is normally generated per respiratory cycle. A respiration-triggered sequence accordingly acquires data of a particular slice of the examination region once per respiratory cycle.

In respiratory triggered MR measurements, the repetition time (TR)—thus the time between two excitations of the same slice—is not fixed, but rather varies with the respiratory cycle of the patient. The repetition time TR is an important contrast-defining parameter in magnetic resonance imaging. A respiratory triggered magnetic resonance imaging, is characterized by an effective repetition time $TR_{e\!f\!f}$ that is equal to the mean respiratory cycle of the patient. The respiratory cycle of the patient is subject to severe individual (and also disease-dependent) fluctuations and typically amounts to between 3 and 6 seconds. Respiratory triggering is therefore preferably used for those sequences in which the desired repetition time TR lies within this range. A few typical examples are T2-weighted imaging with TSE (TSE: Turbo Spin Echo) sequences and diffusion-weighted imaging with spin echo EPI sequences (EPI: "echoplanar imaging").

In the following, an acquisition module designates a partial sequence that is executed to excite an individual slice of the examination region and the subsequent data acquisition of the excited volume. For a complete data acquisition of a slice, multiple acquisition modules of this slice are normally necessary. In respiratory triggering, these modules are executed in different respiratory cycles. In order to achieve an acceptable efficiency in the measurements in spite of the relatively long effective repetition times, successive data of multiple slices (instead of only one) are acquired per respiratory cycle, for example, and thus acquisition modules of different slices are executed during one respiratory cycle. The execution of acquisition modules after a "trigger" is designated as an acquisition phase in the following. The duration of the acquisition phase after an individual "trigger" is designated as an acquisition duration Tac_p. The complete acquisition of the data of a slice normally takes place in multiple acquisition phases.

In the acquisition of image data, it often occurs that nuclear spins of a specific tissue component (fat tissue, for example) emit a strong signal. In comparison to other tissue types, fat tissue thereby appears very intensely in the generated images, such that a correct diagnosis generation can by hindered by this. Therefore, a number of techniques have been developed in order to suppress the signal of fat tissue (for example by spectral saturation). It similarly occurs that nuclear spins in specific regions (for example directly adjacent to the examination region to be examined) emit a signal that interferes with the desired acquisition. Techniques have also already been developed to suppress such signals, for example by spatial saturation.

To suppress such unwanted signals in a data acquisition by means of an acquisition module, one or more preparation modules are (normally) switched before each acquisition module. Each preparation module normally includes a radio-frequency excitation or inversion pulse as well as spoiler gradients to dephase the transverse, unwanted signal components.

In the following, a problem that leads to an insufficient suppression of the unwanted signal (here fat) should be explained in the example of fat suppression with spectrally selective saturation pulses. However, the same or, respectively, a similar problem exists in the suppression of other unwanted signal components or in the suppression of fat with other methods.

Fat delivers a very intensive signal (for example in T2-weighted turbo spin echo images) that can outshine other signals and thus can hinder the finding [assessment] of various illnesses. In MR images that are acquired with EPI sequences, fat is shifted in the phase encoding direction relative to the water component. The shifted fat image interferes with the image impression and can superimpose lesions. To suppress fat signals, the fact can be utilized that the resonance frequency of protons that are bound in fat molecules differs by 3.3-3.5 parts per million (ppm), thus by approximately 217 Hz at 1.5 T, from those protons that are bound in water molecules.

To suppress the fat signals, before each acquisition module a spectrally selective excitation pulse can be switched that flips protons that are bound in fat molecules into the transversal plane and does not affect protons that are bound in water molecules. The fat signal that is excited in such a manner is subsequently dephased with a spoiler gradient. In the acquisition module that is switched (activated) immediately afterward, the fat signal accordingly supplies no contribution or supplies only a strongly reduced signal contribution. The duration of an acquisition module in the aforementioned sequence techniques is in the range of the T1 relaxation time of fat (approximately 260 ms at 1.5 T field strength). A significant portion of the fat protons are consequently aligned parallel to the field again after the execution of the acquisition module. These would deliver a signal contribution in a subsequent acquisition module executed immediately after the first acquisition module. This is avoided by the preparation module being switched again before each acquisition module. The spectrally selective radio-frequency pulse of the preparation module is normally not slice-selective. The repetition time of the preparation modules (TR-FAT in the example) is thus shorter than the repetition times of the slice-selective acquisition modules TR_im_ac.

For optimal fat suppression, the excitation flip angle of the preparation module must be selected depending on the repetition time of the preparation modules, as well as the time between the excitation pulse of the subsequent acquisition module (and the field strength-dependent T1 relaxation time of fat). The optimal flip angle is calculated for a dynamic steady state of the fat spins in which the longitudinal magnetization of the fat spins respectively has the same value immediately before the excitation pulse of a preparation module. However, this steady state does not immediately appear after the first preparation module. Rather, the longitudinal magnetization passes through a transcendental state and only approaches the steady state after a series of preparation modules. The fat suppression in the acquisition modules that are executed after the first preparation modules of the entire sequence is consequently not ideal, meaning that fat is not sufficiently suppressed.

In a magnetic resonance measurement that is not respiratory-triggered, this problem exists only once at the beginning of the measurement. In a respiratory-triggered magnetic resonance measurement, the steady state of the fat protons must reestablish after every trigger—thus during each breathing interval—since fat is nearly completely relaxed in the time interval between the last preparation module of the (n−1)-th acquisition phase (after the (n−1)-th trigger event) and the first preparation module of the n-th acquisition phase (after the n-th trigger), since given a typical breathing interval this time interval is approximately five to ten times as long as the T1 time of fat. In particular, all data of a slice (and consequently the MR images that are calculated from these data) whose acquisition modules are executed relatively early after a trigger (slice S1 in FIG. 1, for example) are insufficiently fat-saturated. This can significantly hinder the diagnosis with the aid of these images.

The terms "respiratory gating" and "respiratory triggering" are not used consistently in the prior art. Within the scope of the present invention, respiratory triggering is used to mean a technique that synchronizes the imaging MR measurement with the breathing of the freely breathing patient and attempts to acquire a predefined packet of measurement data during an comparatively quite phase of the respiratory cycle. If a defined slice is excited only once per trigger, as described above the effective TR of the sequence is thus equal to or a multiple of the mean breathing cycle of the patient.

As used herein, respiratory gating means an MR measurement during which the breathing of the patient is detected and associated with the acquired measurement data, but whose repetition rate (in particular its TR, thus the time between the successive excitation of a slice) is independent of the breathing of the patient. Rather, in the case of respiratory gating the repetition rate is controlled by a (sequence) parameter or by an additional physiological signal (not the breathing!), for example an EKG. For respiratory gating, the breathing information is used to repeatedly acquire individual data packets that were acquired during more significant breathing motion, for example, or to predictively acquire especially motion-sensitive k-space lines or k-space lines determining the image impression in an comparatively quite breathing phase or after a diaphragm position was measured which corresponds to such a phase (for example in ROPE—respiratory ordered phase encoding). The problem illustrated above of the insufficient suppression of unwanted signals accordingly exists predominantly in techniques with respiratory triggering, but not in techniques which use respiratory gating, since there measurement can take place continuously (or quasi-continuously in the case of an EKG-controlled measurement).

A sequence for magnetic resonance imaging with which image data of a subject to be examined are acquired and with which signals of nuclear spins of a defined type are suppressed is known from DE 10 2007 011 807, which includes the following steps:

(a) apply a suppression module to suppress signals of the nuclear spins of the specific type, (b) apply an acquisition module after a wait period (TI) to acquire measurement data, (c) repeat steps (a) and (b) one or more times, respectively after a repetition time (TR), and (d) before steps (a), (b) and (c), apply a spin preparation module that shifts a magnetization of the nuclear spins of the defined type into a steady state that is maintained via the application of the subsequent steps (a), (b) and (c).

Alternatively, instead of the spin preparation module the first suppression module can also be designed there so that it comprises an RF pulse whose flip angle is selected so that the magnetization of the nuclear spins of the defined type is shifted into a steady state.

The nuclear spins of the specific type should thus already be shifted into the steady state before the "nuclear magnetic resonance sequence" (Steps (a), (b) and (c)). However, in practice this does not work sufficiently well.

SUMMARY OF THE INVENTION

An object of the present invention is to provide a method to acquire measurement data of an examination subject to be examined with a magnetic resonance apparatus, in which method the acquisition of the measurement data is triggered by a physiological signal of the examination subject and in which unwanted signal components are suppressed sufficiently well. It is a further object to provide a corresponding magnetic resonance apparatus and an electronically readable data medium to implement such a method with a sufficiently good suppression of unwanted signals.

The above object is achieved by a method according to the invention for the acquisition of measurement data of an examination subject to be examined with a magnetic resonance apparatus, in which the acquisition of the measurement data is triggered via a physiological signal of the examination subject and in which unwanted signal components are suppressed, that includes the steps:

a) detect data points of a physiological signal, b) evaluate a trigger condition depending on the detected physiological data points, c) execute at least one preparation module to suppress unwanted signals in the time period in which the trigger condition has not yet been satisfied, d) after satisfying the trigger condition, start an acquisition phase of predetermined duration, comprising at least two similar preparation modules (such as that described under c)) to suppress unwanted signals and a respective following acquisition module to acquire measurement data, e) after the acquisition phase, repeat steps a) through d) until all desired measurement data of the examination subject have been acquired, wherein a time interval between two successive preparation modules is respectively the same after a first execution of a preparation module in Step c) until the end of the acquisition phase in a subsequent Step d).

By the execution of at least one preparation module so that unwanted signals are already suppressed before the trigger condition to start the acquisition of measurement data is satisfied, thus before the start of an acquisition phase (that starts at the earliest after satisfying the trigger condition), and by maintaining the time interval between two successive preparation modules from the first execution before satisfying the trigger condition until the end of a respective acquisition phase, a dynamic equilibrium of the spins of the unwanted tissue component can already be at least approximately set before the acquisition of the measurement data (for imaging or spectroscopy), and the quality of the suppression of unwanted signals is significantly increased. The unwanted signals are uniformly suppressed in all acquired measurement data, independent of the acquisition order during an acquisition phase.

In all exemplary embodiments, a series of preparation modules that is not physiologically controlled is essentially interleaved with a series of acquisition modules that is physiologically controlled. The fixed time interval between two successive, identical preparation modules is selected outside of an acquisition phase (thus before satisfying the trigger condition) up to the end of the chronologically immediately following acquisition phase, such that it is respectively equal to the time interval between these preparation modules during the acquisition phase.

If multiple different preparation modules are switched before each acquisition module (for example to suppress different unwanted signal components), the fixed time interval between different preparation modules can likewise be selected to be identical to the time interval of these preparation modules during the acquisition phase.

During the acquisition phase, the time interval between two successive identical preparation modules is limited at the lower end by the accumulated duration of different preparation modules and the duration of an acquisition module. If the series of preparation modules that are not physiologically controlled is now considered first, with the temporal arrangement of the preparation modules that was just described respective time gaps that are long enough in order to execute an acquisition module thus exist between two successive identical preparation modules. Immediately before each of these gaps, using the detected physiological breathings signals it is checked whether the trigger condition for the start of an acquisition phase is satisfied. If the trigger condition is not satisfied, no acquisition module is executed in the immediately following gap between two identical preparation modules, and the trigger condition is re-checked immediately before the next gap. Additional physiological data points detected in the intervening time are thereby normally provided. If the trigger condition is satisfied, respective acquisition modules are executed in the following N gaps. N (N≥1) is a predetermined number of acquisition modules that should be acquired per trigger. Each of these N acquisition modules can thereby acquire measurement data of various slices. Normally, no check of the trigger condition is made during this acquisition phase. However, after concluding the acquisition phase, the check of the trigger condition can respectively be continued immediately before a gap between two preparation modules, until the trigger condition is satisfied again, whereby the next acquisition phase is triggered. The entire sequence ends when all measurement data that are required for image reconstruction and/or for a spectroscopy measurement are acquired. This is normally the case after a predetermined number of acquisition phases.

It has long been known that the breathing of the patient can also be detected with MR signals using what are known as navigators or navigator sequences. A navigator is normally a short sequence that acquires MR signals of the diaphragm, for example, from which the breathing phase of the patient can be extracted at the point in time of the acquisition of the navigator signal, for example. In the special case that the breathing of the patient is detected with a navigator, at least one navigator sequence is executed in the gaps between the preparation modules before which the trigger condition was not satisfied. The result of the navigator sequence is normally a physiological signal point. This is then provided immediately before the next gap given the re-checking of the trigger condition.

Different types of preparation modules to suppress unwanted signals in MR measurements are already known which normally include a radio-frequency excitation or inversion pulse (at least one), as well a spoiler gradients to dephase the transverse signal component, and which can be used in the method according to the invention. A few important ones should be noted briefly here.

One group of such preparation modules comprises a spectrally selective excitation pulse (also called a saturation pulse) to suppress signals of nuclei of the examination subject whose resonance frequency has a defined chemical shift as a result of its chemical environment. The primary application in MR imaging here is the already aforementioned fat suppression, in which the chemical shift of protons that are bound to fat molecules relative to those that are bound in water molecules is utilized. In what is known as proton spectroscopy, spectrally selective pulses are also used in the reverse in order to suppress the dominant signal of water relative to (for example) N-acetyl aspartate, citrate, creatine, choline, lactate or other metabolites of interest.

As described above with regard to fat suppression, a spectrally selective excitation pulse that flips protons that are bound in fat molecules into the transversal plane and does not affect protons that are bound in water molecules is hereby switched before each acquisition module. The fat signal that is excited in this manner is subsequently dephased with a spoiler gradient. In the acquisition module switched immediately following this, the fat signal accordingly supplies no signal contribution or only a strongly suppressed signal contribution. The flip angle of the excitation pulse is thereby normally selected to be somewhat greater than 90 degrees, and is selected such that the longitudinal magnetization of the unwanted signal component is zero at the point in time of the excitation pulse of the following acquisition module. The optimal flip angle is calculated for a dynamic steady state of the fat spins in which the longitudinal magnetization of said fat spins has the same respective value immediately before the excitation pulse of a preparation module. The result of this calculation is a function of the repetition time of the preparation modules (TR-FAT), as well as the time between the excitation pulse of the preparation module and the excitation pulse of the following acquisition module, as well as the field strength-dependent T1 relaxation time of fat. In a precise calculation it is additionally to be considered that the (normally not spectrally selective) radio-frequency pulses of the acquisition modules likewise affect the fat signal. However, since these are assumed to be spatially selective here and the breathing interval (and therefore the effective repetition rate of a defined acquisition module; referred to as TR_im_ac later on) is long relative to the T1 relaxation time of fat, this influence here can normally be ignored.

In a variation of the spectral suppression technique that was just described, the spectrally selective excitation pulse just described is replaced with a spectrally selective inversion pulse, with a simultaneous extension of the time period between RF pulse of the preparation module and excitation pulse of the following acquisition module, such that the magnetization of the unwanted signal component is again near zero at the point in time of the excitation pulse of the acquisition module. The advantage is that pulses known as adiabatic radio-frequency pulses can be used that are insensitive to variation of the B1 amplitude. The disadvantage of the inversion variant relative to the saturation variant is the longer duration of the preparation module, as well as the (normally) higher specific absorption rate (SAR).

A third important group of preparation modules is spatially selective saturation pulses to suppress unwanted signals from a specific location. Such a preparation module comprises a spatially selective excitation pulse. However, no slice refocusing gradient is switched after the excitation pulse. Instead of this, spoiler gradients are switched for additional dephasing of the excited signal. In the acquisition module that is switched immediately afterwards, the signal from spins that were located at the location affected by the saturation pulse at the point in time of said saturation pulse delivers no signal contribution, or a strongly suppressed signal contribution. Important applications—for example in axial, abdominal imaging—are two saturation bands parallel to the slices, respectively above and below the imaging volume to be assessed, for example. These suppress inflowing blood that otherwise can lead to pulsation artifacts.

A magnetic resonance apparatus according to the invention has a basic field magnet, radio-frequency antennas to radiate RF pulses and receive echo signals, a gradient system having gradient coils to apply gradient fields, a signal detection device to detect physiological signals, a trigger unit, and a computer that controls the individual system components of the magnetic resonance apparatus corresponding to the method described herein.

The above object also is achieved in accordance with the present invention by a non-transitory, computer-readable data storage medium that is encoded with programming instructions (program code) that, when the storage medium is loaded into a computerized control and evaluation system of a magnetic resonance apparatus, cause the control and evaluation system to operate the magnetic resonance apparatus according to any or all of the above-described embodiments.

The advantages and embodiments described with regard to the method apply analogously to the magnetic resonance apparatus and the electronically-readable data storage medium.

DESCRIPTION OF THE PREFERRED EMBODIMENTS

Figure 1:
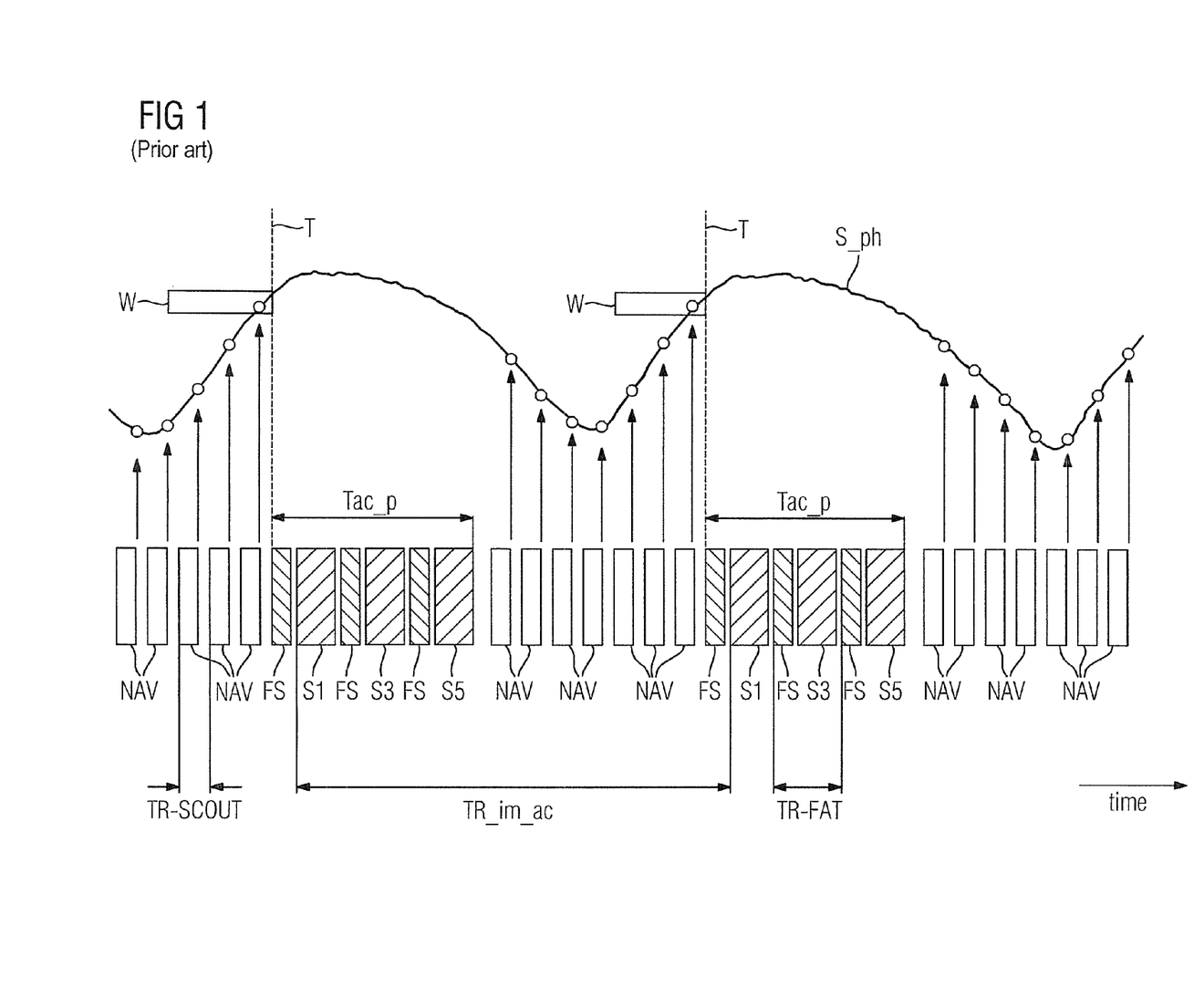
FIG. 1 schematically illustrates a sequence of a respiratory-triggered MR measurement according to the prior art.

FIG. 1 schematically shows the chronological workflow of an example of a sequence of a respiratory-triggered MR measurement. A navigator sequence NAV is initially repeated with constant time interval TR-SCOUT. The result of each navigator measurement is a physiological data point (represented as a circle) that, for example, corresponds to a diaphragm position and thus reflects the breathing movement. The solid line S_ph that connects the measured data points (circles) serves to better visualize the underlying movement and therefore is shown solid, although only the measured data points shown as circles are actually present in the examination. Instead of the detection of the physiological data points by means of what is known as a navigator sequence, the physiological signal (here: breathing signal) can also be detected by means of an external sensor (for example a breathing cushion or a breathing belt) that can be connected with the magnetic resonance apparatus. In this case, the physiological data points can be detected continuously over the entire measurement duration. However, it is already sufficient to consider only those physiological data points in the time periods after the acquisition phase up to a following satisfaction of the trigger condition.

As soon as a selected trigger condition is satisfied, a trigger T is generated (also called a "trigger event"). As a result of the trigger event, no further navigator sequences NAV are executed; rather, instead of this an imaging (or also spectroscopic) sequence is started which acquires a first measurement data packet. The sequence acquiring the measurement data here comprises a sequence of preparation modules FS and acquisition modules S1, S3, S5. The preparation modules FS are identical; the acquisition modules S1, S3 and S5 can respectively acquire a different slice of the examination region to be examined. This progression of the sequence acquiring measurement data requires a predetermined time interval ("acquisition duration") Tac_p and is designated in the following as an acquisition phase. After an acquisition phase, a short fill time period can be inserted in which no manipulation of the nuclear spins in the examination region is implemented and which serves so that the disruption of the magnetization due to the sequence acquiring measurement data (which disruption can affect a subsequent measurement by means of an additional navigator sequence NAV) at least partially decays.

After this, physiological data points are again determined (via navigator sequences NAV, for example) until the cited trigger condition is satisfied another time during the next breathing interval of the patient. The satisfaction of the trigger condition in turn stops the execution of navigator sequences via an additional trigger T and initiates an additional acquisition phase during which an additional measurement data packet is acquired. This workflow is repeated until all desired image or spectroscopy data of the examination region are acquired. A trigger is generated if multiple conditions are satisfied, for example. One condition can be that the series of measured physiological data points (circles) is rising. With the algebraic sign convention that is used here, this means that the patient exhales. An additional trigger condition can be that the measured physiological data point falls within a pre-established acceptance window W. The position of such an acceptance window W can be established at the end of an initial learning phase in which the physiological movement was observed, for example. Such a learning phase is not shown here. During such a learning phase, the navigator sequence can (for example) be repeated with constant time interval TR-SCOUT without an interruption by an imaging sequence.

The time between two successive preparation modules FS during the acquisition phase of duration Tac_p is indicated as TR-FAT in FIG. 1. During the acquisition phase, this time interval TR-FAT is constant, such that the spins of the unwanted tissue component (fat in the example) approaches a dynamic steady state. However, this is abruptly interrupted with the conclusion of the acquisition phase. The time between the last preparation module FS of an acquisition phase and the first preparation module FS of the following acquisition phase is normally significantly longer than TR-FAT, such that the dynamic steady state of the spins of the unwanted tissue component must first be re-established. As was presented in detail above, the consequence is an insufficient suppression of the signals of the spins of the unwanted tissue component, at least in the first slices acquired by the acquisition modules, in particular the slice that is respectively acquired by the first acquisition module of an acquisition phase (thus in particular slice S1 in FIG. 1).

The time which passes between the successive excitations of the desired nuclear spins (for example those of protons bound to water) of a specific slice is designated as TR_im_ac in FIG. 1. In the limiting case of an ideal periodic breathing, this time TR_im_ac would be constant and a dynamic steady state could arise. Any real breathing is not perfectly periodic, however, such that the current TR_im_ac is subject to a certain fluctuation. A regular breathing pattern is termed a "quasi-periodic movement" and the state of the nuclear spins of the desired tissue components (for example of the protons bound to water) after the initial transcendent state is designated as "quasi-dynamic steady state". Furthermore, the T1 time of the tissue components that are of the most interest is short relative to a typical breathing cycle, such that the spins can nearly completely relax between two excitations. Only free water with an extremely long T1 time (which is not addressed further here, however) forms an exception.

It is again stressed that FIG. 1 is a schematic representation. In particular, the scaling of the time axis is not realistic: the duration of an acquisition module for the sequence types that are relevant here is typically between 30 ms and 200 ms; the duration of a preparation module is between 20 ms and 60 ms. The acquisition duration is typically selected between 25% and 50% of the respiratory interval. The respiratory triggering interval of a patient is typically three to six seconds. The acquisition duration can accordingly typically amount to between less than one second and up to three seconds. The number of preparation modules FS and acquisition modules S1, S3, S5 executed per trigger T (and therefore per respiratory interval or, respectively, per acquisition phase) is thus normally significantly greater than three as is shown here. For example, given an acquisition duration of 1200 ms, a duration of an acquisition module S1, S3, S5 of 90 ms, and a duration of a preparation module FS of 30 ms, ten preparation modules FS and accordingly ten acquisition modules (for example S1, S3, S5, S7, S9, S11, S13, S15, S17, S19; not shown) can be executed, for example.

Figure 2:
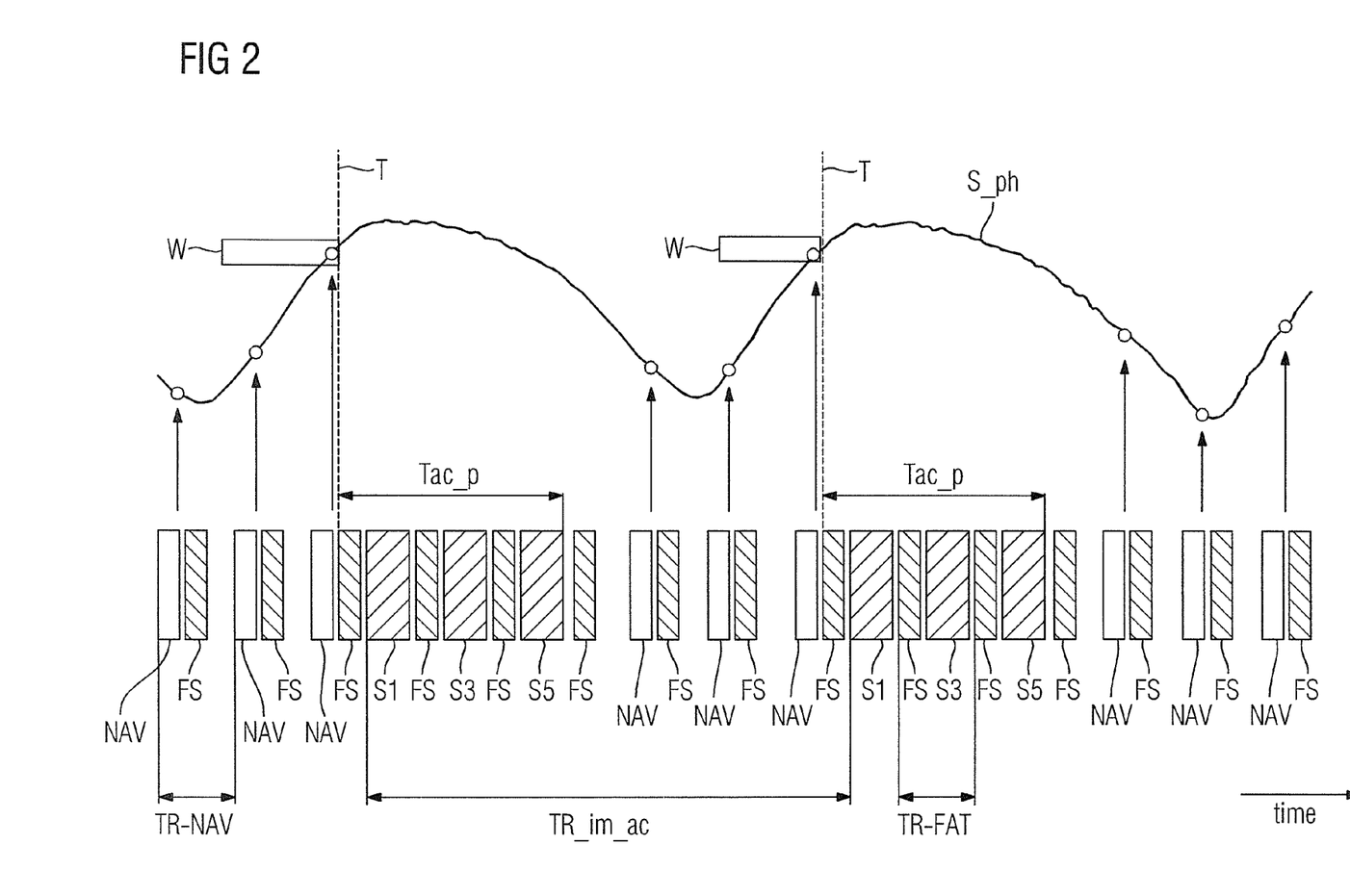
FIG. 2 schematically illustrates an embodiment of a sequence of a respiratory-triggered MR measurement according to the invention.

FIG. 2 shows a schematic representation of the chronological workflow of a sequence according to the invention that implements the method according to the invention, which representation is analogous to FIG. 1.

In contrast to FIG. 1, here preparation modules FS are executed from the start with constant time interval TR-FAT from one another during the complete running time of the sequence. During the acquisition phase, the time interval between two successive preparation modules is limited at the low end by the duration of the interposed acquisition module. This minimum time interval can be used to determine TR-FAT. Because of the continuous execution of preparation modules with constant time interval TR-FAT, the dynamic steady state of the spins of the unwanted tissue component is not interrupted after conclusion of an acquisition phase and does not need to be reestablished at the beginning of the next acquisition phase. This in particular already applies to the very first acquisition phase since preparation modules FS are also executed during the measurement of the physiological data in the search for the first satisfaction of the trigger condition. It is also conceivable that the preparation modules FS are already executed during an initial learning phase (already mentioned above; not shown). Insofar as the detection of the physiological signal takes place with a navigator sequence (as in the example of FIG. 2), this is even recommended since the preparation module also possibly affects the navigator signal and this influence should be kept constant.

By already executing the preparation modules with a constant time interval before the acquisition phase and up to the end of the acquisition phase, unwanted signals of nuclear spins of an unwanted tissue component are suppressed equally well in all slices, independent of the time position of the associated acquisition module S1, S3, S5 in the acquisition phase.

In known methods, with each detection of a physiological data point of the respiratory signal it is normally checked whether the trigger condition is satisfied. Possible trigger points thus lie on a time grid that is predetermined by the time period of the physiological data acquisition. Given a detection of the physiological data points by means of an external physiological sensor (for instance a breathing cushion or belt), this time period amounts to approximately 20 ms, for example; given the detection of the respiratory signal with navigator sequences, this time period is limited at the lower end by the duration of a navigator sequence. A navigator sequence lasts between a few milliseconds and 100 ms, depending on the navigator technique that is used.

In the method according to the invention it is taken into account that the execution of acquisition modules S1, S3, S5, . . . can be started only in a gap of the series of preparation modules FS that is not physiologically controlled, since both the time between two identical preparation modules FS and the time between a preparation module FS and the following acquisition module S1, S3, S5, . . . during the acquisition phase is fixed. Possible trigger points thus lie on a time interval that is determined by the time between two successive, identical preparation modules FS (to suppress the same unwanted signal component). In FIG. 2, the time interval thus corresponds to TR-FAT. This time interval is limited at the lower end by the accumulated duration of the various preparation modules FS and the duration of an individual acquisition module S1, S3, S5 and must be short relative to the respiratory interval (corresponding to TR_im_ac) so that the method according to the invention can be used. The latter is the case for most MR sequences used in connection with respiratory triggering techniques, and in particular in the aforementioned examples of a T2-weighted imaging with TSE and diffusion-weighted imaging with spin echo EPI.

If the physiological signal (here the breathing) is detected with navigators, the time interval between a navigator sequence NAV and a preceding preparation module FS should advantageously be constant. This is particularly the case if at least one of the preparation modules that is used is not selective, or if the excitation volume of the navigator sequence NAV and that of a selective preparation module intersect, since then the preparation module also affects the navigator signal NAV. It thus results that the time interval between two navigators TR-NAV is equal to the time interval between two preparation modules. The physiological signal is normally obtained via the comparison of a current navigator measurement with an earlier reference measurement. It is assumed that all signal changes between the two navigator measurements are the result of the physiological movement. The time interval between a navigator measurement and a particular preparation module (to suppress a particular unwanted signal component) must consequently also be kept constant. Otherwise, a varying signal contribution of the unwanted component in the navigator signal would be obtained that would incorrectly be interpreted as signal changes as a result of the physiological movement.

From this it follows that the time period TR-NAV with which the physiological signal is detected is preferentially defined (under the cited requirements) by the time between two identical preparation modules FS to suppress the same unwanted signal component.

In the case in which the physiological signal is detected with a navigator, in the time intervals before the trigger condition is satisfied at least one (exactly one in the example presented in the figures) navigator sequence NAV is executed in the gaps between two respective preparation modules FS. This assumes that the duration of a navigator sequence NAV is short enough in order to be executed during the cited gaps. Stated in a different way: the duration of a navigator sequence NAV must be shorter than or identical in length to the duration of an acquisition module S1, S3, S5, . . . Navigator sequences NAV are normally very short, and the condition is satisfied. If it is not satisfied, the gap (thus the time between identical preparation modules FS) can be extended accordingly. However, the duration of the acquisition phase Tac_p is thereby necessarily extended (given a constant number N of acquisition modules per acquisition phase; N=3 in FIG. 2). Since the duration of the acquisition phase Tac_p is normally selected relative to the respiratory interval TR_im_ac of the patient, the duration of the acquisition phase can be reduced again by reducing the number N of acquisition modules per acquisition phase. The number of acquisition phases that is necessary in order to acquire all data (and therefore the measurement duration) is thereby normally extended. Furthermore, the optimal flip angle of the preparation modules is adapted as necessary to the new repetition time TR-FAT.

In the workflow shown in FIG. 2, the trigger condition is checked immediately after the execution of a navigator, and not only (as described above with reference to the prior art) after the preparation module following a navigator (thus immediately before a gap). In the case that for the detection of the breathing a navigator is used this is equivalent since no additional information about the respiratory state of the patient is present at a later point in time.

Figure 3:
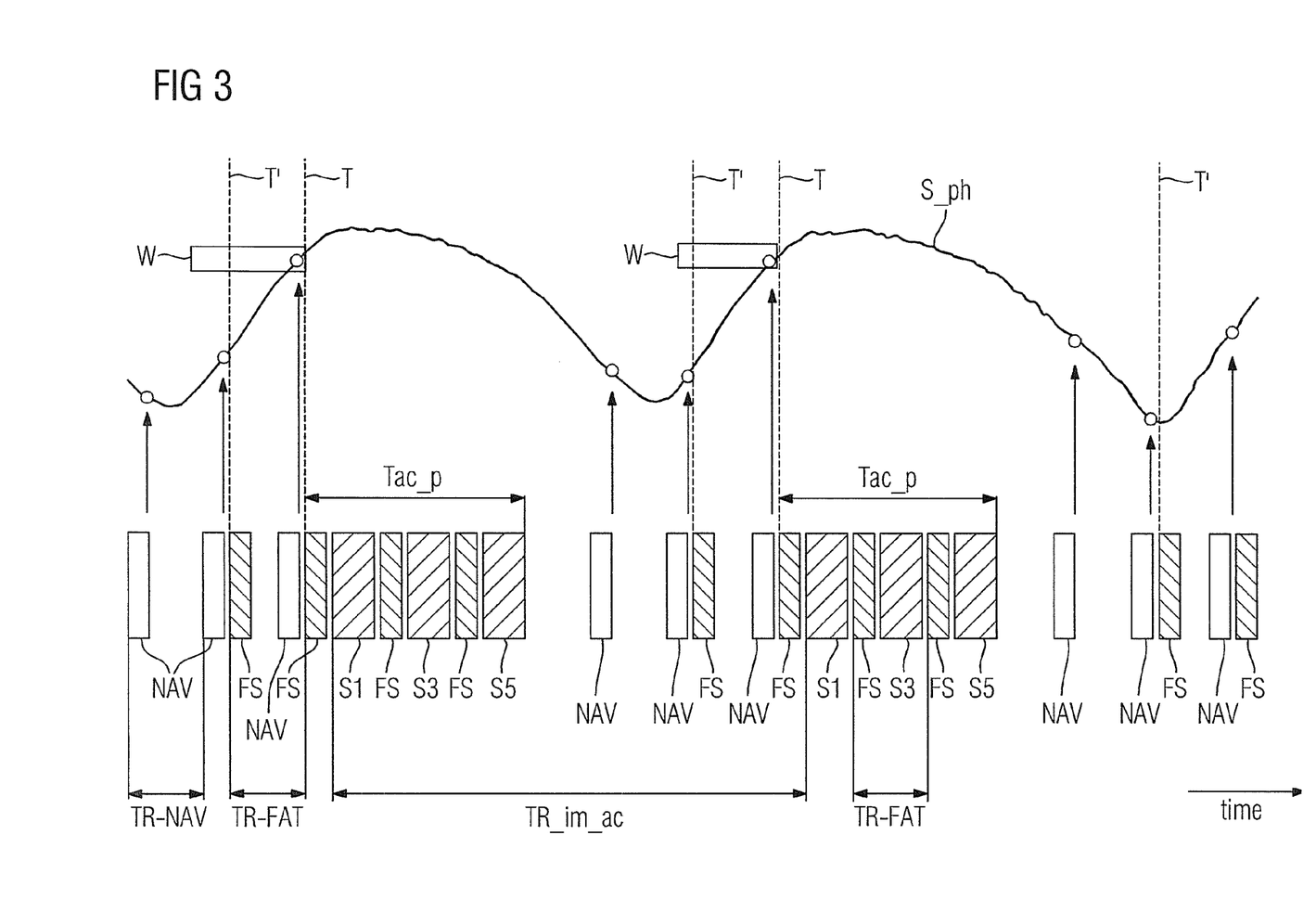
FIG. 3 schematically illustrates another embodiment of a sequence of an additional possible sequence of a respiratory-triggered MR measurement according to the invention.

FIG. 3 shows an additional principle, schematic representation of the chronological workflow (analogous to FIG. 1) of a sequence according to the invention that implements the method according to the invention.

In contrast to FIG. 2, however, the preparation modules FS are not switched continously; rather, initially only physiological data points are detected with a respective navigator sequence NAV, for example as in the representation.

The first preparation module FS is executed before satisfaction of the trigger condition for the trigger T, but only after an additional condition (T') is satisfied. After this additional condition is satisfied (T'), preparation modules are executed in turn with constant time interval TR-FAT until the end of a subsequent acquisition phase so that a dynamic steady state of the unwanted signal component can arise. The satisfaction of the additional condition can be checked depending on the currently detected physiological signals and/or depending on predetermined temporal thresholds. For example, it is conceivable to perform a check in the detected physiological data points when the point in time "maximum inspiration achieved" is reached, for example by falling below an indicated minimum value or detecting a rise of the values of the physiological data points after a preceding decline, and then—thus at the beginning of the phase of the inspiration, for example—to trigger the first preparation module FS before an acquisition phase. Alternatively or additionally, the condition T' to be satisfied can require that a certain time duration has elapsed after the end of an acquisition phase, for example, after which a preparation module FS should be executed again before a next acquisition phase. Such a temporal threshold can take into account the mean respiratory phase TR_im_ac and the (predetermined) duration of an acquisition phase Tac_p, for example, and thus ensure that a series of temporally equidistant preparation modules FS is begun again after an acquisition phase before a next trigger T to start a new acquisition phase is to be expected. In this exemplary embodiment, a series of preparation modules executed with a constant time interval is thus always triggered again via satisfaction of the additional condition (T'). Although this additional condition can be related to physiological values, the series is nevertheless not viewed as "physiologically controlled" in the actual sense since it does not inevitably need a physiological control in order to achieve the desired result. For example, a mere time boundary is sufficient for the additional condition.

The SAR exposure of the examined examination subject (a patient, for example) is reduced via the interruption of the execution of preparation modules in this exemplary embodiment after an acquisition phase.

Moreover, the exemplary embodiment of FIG. 3 essentially proceeds as in FIG. 2. However, the trigger condition should include as an additional condition that, after the last preparation module FS (before the trigger condition of trigger T is satisfied), exactly the time period TR-FAT elapses before an additional preparation module FS is now triggered by a trigger T with regard to an acquisition phase. This can be achieved as follows: After the additional trigger condition T is satisfied a first preparation module FS is executed. If the trigger condition is not satisfied after execution of the first preparation module FS, no acquisition module is executed in the immediately following gap between two preparation modules FS; rather, the trigger condition is re-checked immediately before the next such gap. If the trigger condition is satisfied, an acquisition phase is begun in which measurement data of the examination subject are acquired. Thereby, if the physiological motion is detected with a navigator the navigator sequence is executed in the gap between two FS modules, if the trigger condition of trigger T is not satisfied immediately before the gap. The time interval between two successive preparation modules FS in a time period that begins with the satisfaction of the additional condition and ends with the end of the following acquisition phase is constant (and here is equal to TR-FAT), independent of whether the actual trigger condition for the trigger T has already been satisfied (the measurement is thus located in an acquisition phase) or not. In the shown example, an acquisition phase comprises three acquisition modules S1, S3, S5 which are executed after the trigger T in the three gaps between the preparation modules FS.

After concluding an acquisition phase, in this embodiment again no preparation modules FS are initially executed; rather, these are only executed again after satisfying the cited additional condition (T'). The number of preparation modules FS that are executed in total—and therefore the SAR exposure—is thus reduced relative to the exemplary embodiment of FIG. 2.

In spite of this, before each acquisition phase at least one preparation module FS is executed, whereby a dynamic steady state of the spins of the unwanted tissue component is already approximately achieved at the point in time of the trigger T starting the acquisition phase. As was already stated above with regard to FIG. 2, the representation in Figures here is only schematic, and far more navigators NAV (and therefore detected physiological data points) and preparation modules FS as well as acquisition modules S1, S3, S5 can actually be executed in a respiratory cycle than are shown. In the example cited above with a respiratory interval of a patient from three to six seconds and an acquisition duration of 1200 ms, a duration of an acquisition module S1, S3, S5 of 90 ms, and a duration of a preparation module FS of 30 ms, depending on the selection of the additional condition two to five preparation modules can easily be executed after the satisfaction of the additional condition (T') and before the satisfaction of the trigger condition (T).

In each exemplary embodiment, instead of the shown navigator sequence NAV an external sensor can be used that can be connected with the magnetic resonance apparatus, which external sensor (for example a breathing cushion or a breathing belt which detect the physiological breathing movement via pneumatic, hydraulic or piezoelectric sensors) can be used in order to detect the physiological data points. Possible influences between the preparation modules and the detection of physiological data points via navigators can be made irrelevant in this way.

Figure 4:
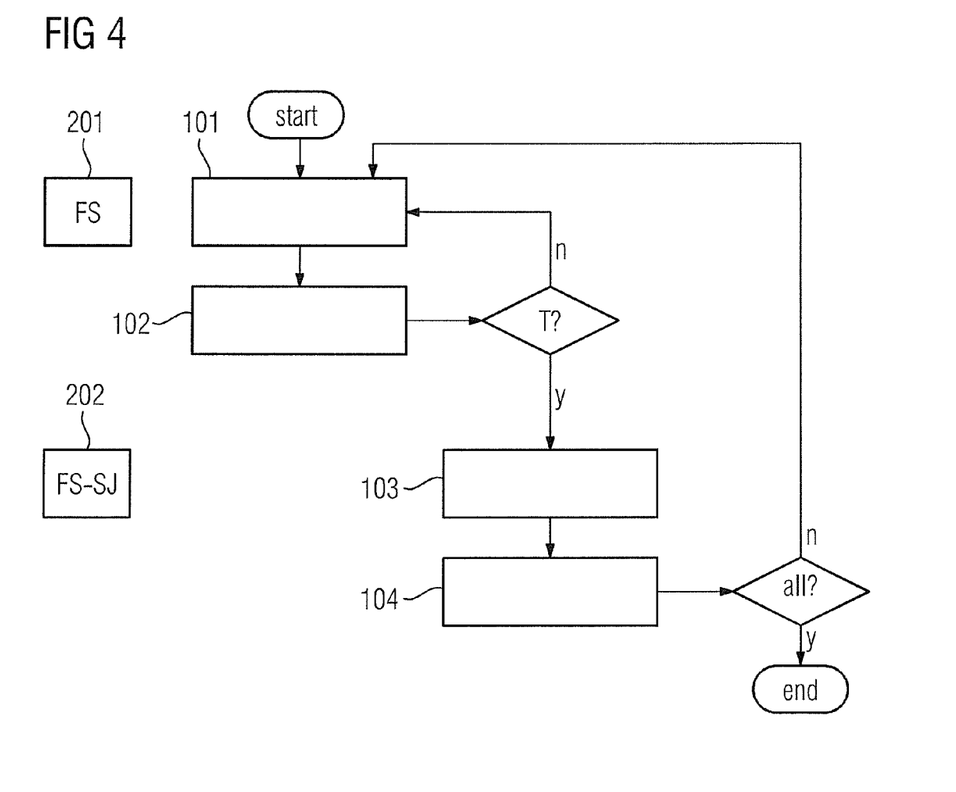
FIG. 4 is a flowchart of an embodiment of a method according to the invention.

FIG. 4 shows a schematic workflow diagram of the method according to the invention. After the start ("start") of the method, a physiological signal (the respiratory signal, for example) is initially measured by means of a signal detection device (Block 101) and corresponding physiological data points 102 are detected. During the detection of the physiological data points 102, at least one preparation module ("FS") is switched to suppress unwanted signals. Optionally, the switching of the at least one preparation module in this phase is controlled via an additional condition (see FIG. 3, T'). A trigger condition is checked ("T?") depending on the detected physiological data points 102. If the trigger condition ("T?") is not satisfied (n), physiological data points 102 continue to be detected. However, if it is satisfied (y), an acquisition phase (103) is started in which at least one preparation module ("FS")—similar to the preparation module ("FS") executed outside of the acquisition phase during the detection of the physiological data points—to suppress unwanted signals and a following acquisition module ("Sj") are executed. Measurement data 104 of the examination subject are acquired by means of the acquisition module ("Sj"), which measurement data 104 are stored. If all desired measurement data have already been acquired ("all?"—y), the method ends ("end"). If all desired measurement data have not been acquired yet ("all?"—n), physiological data points 102 are detected again or given the use of an external sensor which continuously detects physiological data points (for example) these are compared again with the trigger condition ("T?") (Block 101) until the trigger condition ("T?") is satisfied and a new acquisition phase 103 with at least one acquisition module Sj and associated preparation module FS begins etc.

Figure 5:
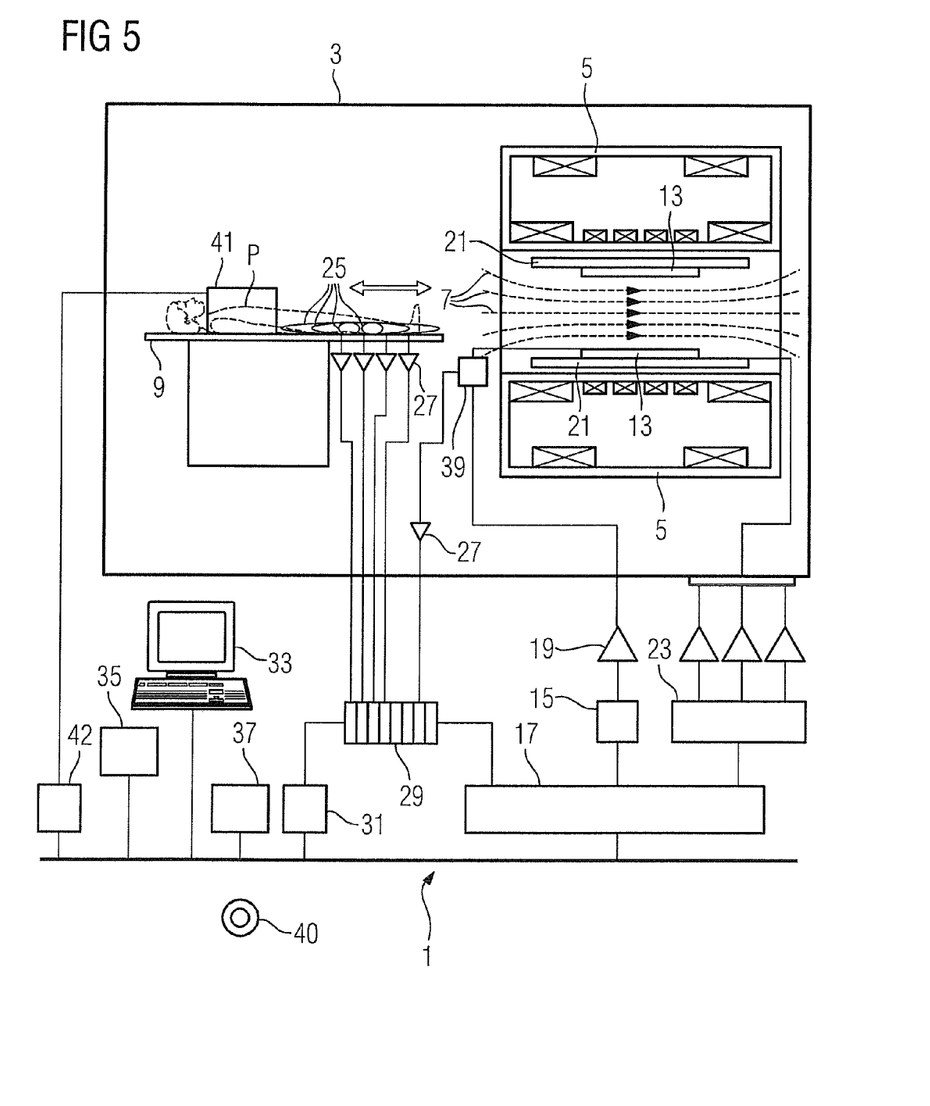
FIG. 5 schematically illustrates an MR apparatus operable to implement any or all embodiments of the method according to the invention.

FIG. 5 schematically shows the design of a magnetic resonance apparatus 1 with its essential components. In order to examine a body by means of magnetic resonance imaging, various magnetic fields matched to one another as precisely as possible in terms of their temporal and spatial characteristics are radiated towards the body or, respectively, switched.

A strong magnet (typically a cryomagnet 5 with a tunnel-shaped opening) that is arranged in a radio-frequency-shielded measurement chamber 3 generates a static, strong basic magnetic field 7 that typically amounts to 0.2 Tesla to 7 Tesla or more. An examination subject, a body or a body part to be examined—represented here as patient P—is borne on a patient bed 9 that can be moved continuously through the measurement volume of the magnetic resonance apparatus and is driven into the homogeneous region of the basic magnetic field 7 (measurement volume).

Magnetic resonance apparatuses with a bearing device (a patient bed, for example) that can be driven into and out of a patient bore of the magnetic resonance apparatus automatically by means of a drive device, which patient receptacle is permeated by a magnetic field of the magnetic resonance apparatus, are known for the acquisition of magnetic resonance images. Since the patient bore frequently has quite a small diameter, the patient is placed on the patient bed outside of the patient bore, after which the patient bed can be driven automatically into the patient bore by means of the drive device.

The excitation of the nuclear spins of the body takes place with radio-frequency magnetic pulses (RF pulses) that are radiated via a radio-frequency antenna (shown here as a body coil 13). The radio-frequency excitation pulses are generated by a pulse generation unit 15 that is controlled by a pulse sequence control unit 17. After an amplification by a radio-frequency amplifier 19, they are conducted to the radio-frequency antenna. The radio-frequency system is only schematically indicated. More than one pulse generation unit 15, more than one radio-frequency amplifier 19 and multiple radio-frequency antennas are typically used in a magnetic resonance apparatus 1.

Furthermore, the magnetic resonance apparatus 1 possesses gradient coils 21 with which magnetic gradient fields are superimposed on the basic magnetic field, for example for selective slice excitation and for spatial encoding of the measurement signal. The gradient coils 21 are controlled by a gradient coil control unit 23 that, like the pulse generation unit 15, is connected with the pulse sequence control unit 17. The pulse sequence control unit 17 is fashioned such that a pulse sequence according to the invention can be generated.

The signals emitted by the excited nuclear spins are received by the body coil 13 and/or by local coils 25, amplified by associated radio-frequency preamplifier 27, and further processed and digitized by a receiver unit 29.

Given a coil that can be operated both in transmission mode and reception mode (such as the body coil 13, for example), the correct signal relaying is regulated by an transmission/reception diplexer 39.

A image processing unit 31 generates from the measurement data an image that is presented to a user via a control panel 33 or is stored in a memory unit 35.

A signal detection device 41 to detect physiological signals of the examination subject P is connected with a trigger unit 42 of the magnetic resonance apparatus to evaluate the detected physiological data points and compare these with trigger conditions, as well as to insert a "trigger" signal upon satisfaction of a selected condition. The signal detection device is not needed if the physiological signal is detected by means of a navigator. In this case the trigger unit can be realized by software on the image processing unit 31 or the central computer 37 or the sequence control unit 17.

A central computer 37 controls the individual system components, in particular for and during the acquisition of the measurement data. The central computer 37 is fashioned such that a method according to the present invention can be implemented. For example, for this purpose a computer program for implementing the method according to the invention can be loaded into or embodied in the computer 37 so as to be executable. The computer program can be stored as encoded instructions (code) on an electronically readable data medium (for example a DVD 40) such that the encoded instructions can be read from the DVD 40 and executed by the central computer 37.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance data from an examination subject wherein unwanted signal components are suppressed, comprising:
   (a) acquiring a physiological signal from an examination subject located in a magnetic resonance data acquisition unit, and detecting data points of said physiological signal;
   (b) in a computerized processor, evaluating a trigger condition dependent on the detected physiological data points;
   (c) operating said data acquisition unit to execute at least one preparation module that suppresses unwanted signals in a time period in which said data points of said physiological signal are still being acquired thus said trigger condition has not yet been satisfied;
   (d) after said trigger condition is satisfied, operating said magnetic resonance data acquisition unit by starting a data acquisition phase of a predetermined duration, comprising at least two preparation modules substantially corresponding to the at least one preparation module implemented in (c), to suppress unwanted signals, followed by a data acquisition module in which magnetic resonance measurement data are acquired; and
   (e) after said acquisition phase, repeating (a) through (d) until all desired magnetic resonance measurement data of the examination subject have been acquired, while maintaining a same time interval between any two successive preparation modules, said time interval starting after said at least one preparation module in (c) and continuing until an end of the acquisition phase in (d).

2. A method as claimed in claim 1 comprising operating said magnetic resonance data acquisition unit with said same time interval between any two successive preparation modules continuously from activating said at least one preparation module in (c) before a first acquisition phase, until complete acquisition of all desired magnetic resonance measurement data from the examination subject.

3. A method as claimed in claim 1 comprising requiring satisfaction of a predetermined condition after an end of an acquisition phase before executing an additional first preparation module of a series of preparation modules with said same time interval.

4. A method as claimed in claim 3 comprising checking an additional condition dependent on currently detected physiological data points or dependent on predetermined temporal boundaries.

5. A method as claimed in claim 1 comprising acquiring said magnetic resonance data respectively from different slices of the examination subject in the respective data acquisition modules of an acquisition phase.

6. A method as claimed in claim 1 comprising detecting said physiological data points with an external sensor connected with said magnetic resonance data acquisition unit.

7. A method as claimed in claim 1 comprising detecting said physiological data points by operating said magnetic resonance data acquisition unit with a navigator sequence.

8. A method as claimed in claim 7 comprising maintaining a constant time interval between said navigator sequence and a preceding preparation module.

9. A method as claimed in claim 1 comprising, in each preparation module, radiating at least one spectrally selective saturation pulse.

10. A method as claimed in claim 1 comprising, in each preparation module, radiating at least one spectrally selective inversion pulse.

11. A method as claimed in claim 1 wherein each preparation module is spatially selective and is configured to suppress signals at a specific location with respect to the examination subject.

12. A magnetic resonance apparatus for acquiring magnetic resonance data from an examination subject wherein unwanted signal components are suppressed, comprising:
   a magnetic resonance data acquisition unit; and
   (a) a control unit configured to acquire a physiological signal from an examination subject located in a magnetic resonance data acquisition unit, and detecting data points of said physiological signal, (b) evaluate a trigger condition dependent on the detected physiological data points, (c) operate said data acquisition unit to execute at least one preparation module that suppresses unwanted signals in a time period in which said data points of said physiological signal are still being acquired thus said trigger condition has not yet been satisfied, (d) after said trigger condition is satisfied, operate said magnetic resonance data acquisition unit by starting a data acquisition phase of a predetermined duration, comprising at least two preparation modules substantially corresponding to the at least one preparation module implemented in (c), to suppress unwanted signals, followed by a data acquisition module, in which magnetic resonance measurement data are acquired, and (e) after said acquisition phase, repeat (a) through (d) until all desired magnetic resonance measurement data of the examination subject have been acquired, while maintaining a same time interval between any two successive preparation modules, said time interval starting after said at least one preparation module in (c) and continuing until an end of the acquisition phase in (d).

13. A non-transitory, computer-readable data storage medium encoded with programming instructions, said data storage medium being loaded into a computerized control and evaluation system of a magnetic resonance apparatus comprising a magnetic resonance data acquisition unit, and said programming instructions causing said computerized control and evaluation system to:
   a) acquire a physiological signal from an examination subject located in a magnetic resonance data acquisition unit, and detecting data points of said physiological signal;
   (b) evaluate a trigger condition dependent on the detected physiological data points;
   (c) operate said data acquisition unit to execute at least one preparation module that suppresses unwanted signals in a time period in which said data points of said physiological signal are still being acquired thus said trigger condition has not yet been satisfied;
   (d) after said trigger condition is satisfied, operate said magnetic resonance data acquisition unit by starting a data acquisition phase of a predetermined duration, comprising at least two preparation modules substantially corresponding to the at least one preparation module implemented in (c), to suppress unwanted signals, followed by a data acquisition module in which magnetic resonance measurement data are acquired; and
   (e) after said acquisition phase, repeat (a) through (d) until all desired magnetic resonance measurement data of the examination subject have been acquired, while maintaining a same time interval between any two successive preparation modules, said time interval starting after said at least one preparation module in (c) and continuing until an end of the acquisition phase in (d).

* * * * *